(12) United States Patent
Sun et al.

(10) Patent No.: US 8,324,482 B2
(45) Date of Patent: Dec. 4, 2012

(54) TRANSGENIC PLANTS

(75) Inventors: Jindong Sun, St. Charles, MO (US);
Kimberly Zobrist, Greenville, IL (US);
Jingrui Wu, Chesterfield, MO (US);
Changlin Fu, Chesterfield, MO (US);
Stanton B. Dotson, Chesterfield, MO (US); Linda Lutfiyya, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 12/972,782

(22) Filed: Dec. 20, 2010

(65) Prior Publication Data

US 2011/0099655 A1   Apr. 28, 2011

Related U.S. Application Data

(62) Division of application No. 10/783,710, filed on Feb. 21, 2004, now Pat. No. 7,888,557.

(60) Provisional application No. 60/449,054, filed on Feb. 22, 2003.

(51) Int. Cl.
*C12N 15/82* (2006.01)
*A01H 5/10* (2006.01)

(52) U.S. Cl. .................. 800/320.1; 800/278; 800/298; 800/300

(58) Field of Classification Search .................. None
See application file for complete search history.

(56) References Cited

FOREIGN PATENT DOCUMENTS

| | | |
|---|---|---|
| EP | 1230345 | 6/2008 |
| WO | 02/15675 | 2/2002 |

OTHER PUBLICATIONS

Cataltepe et al 2007, Eleventh Annual International Conference on Research in Computational Molecular Biology, San Francisco Bay Area; Apr. 21-25, 2007, Protein Function Prediction Using Motifs, Sequence Features, Alignment Scores.*
Hill et al 1998, Biochemical and Biophysical Research Communications 244: 573-577.*
Aravind et al 1998, Nucleic Acids Research 26(19): 4413-4421.*
Aoyama et al., "Ectopic Expression of the Arabidopsis Transcriptional Activator Athb-1 Alters Leaf Cell Fate in Tobacco", The Plant Cell, 1995, pp. 1773-1785, vol. 7.

* cited by examiner

*Primary Examiner* — David H Kruse
(74) *Attorney, Agent, or Firm* — Thompson Coburn LLP; Charles P. Romano

(57) ABSTRACT

Disclosed herein are transgenic plants having recombinant DNA which expresses a G1073 transcription factor which provides enhanced resistance and/or tolerance to water deficit. More specifically the DNA constructs comprise a polynucleotide which encodes at least a functional part of a G1073 transcription factor or a homologous transcription factor.

11 Claims, 1 Drawing Sheet

Alignment Of Conserved Amino Acid Sequences

```
SEQ ID NO:7   AKPPIIVTRDSPNALRSHVLEVSPGADIVESVSTYARRGRGVSVLGGNGTVSNVTLRQ           VVTLHGRFEILSLTGTVLPPPAPPGAGGLSIFLAGGQGQV
SEQ ID NO:8   PKPPTIITRDSPNVLRSHVLEVTSGSDISEAVSTYATRGCGVCIISGTGAVTNVTIRQ           VITLHGRFDILSLTGTALPPPAPPGAGGLTVYLAGGQGQV
SEQ ID NO:9   PKSPIIVARDSPNSLRSHVLEISSGSDIVDSVWGYARRGRGVCVLSGTGAVTNVTLRQ           VVTLHGRFEILSLTGTSLPPPAPPGAGGLTVYLAGVQGQV
SEQ ID NO:10  PKPPIIVTRDSPNALHSHVLEVAGGADVVDCVAEYARRGRGVCVLSGGGAVVNVALRQ           VATLRGRFEILSLTGTVLPPPAPPGASGLTVFLSGGQGQV
SEQ ID NO:11  --K-P-I---RDSPN-L-SHVLE----G-D-----V--YA-RRG-GV-----G-G-V-NV--RQ------ V--TL-GRF-ILSLTGT-LPPPAPPGA--GL----LAG-QGQV
```

TRANSGENIC PLANTS

REFERENCE TO RELATED APPLICATIONS

This application is a divisional of U.S. patent application Ser. No. 10/783,710, filed Feb. 21, 2004 and incorporated herein by reference in its entirety, which claims priority to U.S. Provisional Application 60/449,054 filed Feb. 22, 2003, incorporated herein by reference in its entirety.

JOINT RESEARCH STATEMENT

The claimed invention, in the field of functional genomics and the characterization of plant genes for the improvement of plants, was made by or on behalf of Mendel Biotechnology, Inc. and Monsanto Company as a result of activities undertaken within the scope of a joint research agreement in effect on or before the date the claimed invention was made.

INCORPORATION OF SEQUENCE LISTING

The sequences in the enclosed Sequence Listing are identical to the sequences in the Sequence Listing and computer readable form of prior U.S. Provisional Application 60/449, 054 filed Feb. 22, 2003, which contain the file named "G1073FINAL.ST25.txt" which is 21 kb and was created on 21 Feb. 2003 and which is incorporated herein by reference.

FIELD OF THE INVENTION

Disclosed herein are DNA useful for producing transgenic plants and seeds and methods of making and using such transgenic plants and seed.

BACKGROUND OF THE INVENTION

Water deficit can have adverse effects on plants such as yield reductions, increased susceptibility to disease and pests, reduced plant growth and reproductive failure. An object of this invention is to provide plants which can express genes to ameliorate the adverse effects of water deficit. Useful genes for expression especially during water deficit are genes which promote aspects of plant growth or fertility, genes which impart disease resistance, genes which impart pest resistance, and the like.

Considering the complexity of water use in land plants, especially during conditions that produce water deficit, relatively few genes specifically associated with this aspect of physiology have been identified. It would be of benefit to the art to increase the number and variety of genes involved in regulating water use in plants, more particularly, in corn plants, and even more particularly in corn plants experiencing water deficit. It would be especially advantageous to identify transcription factors which can be used in directing the production of proteins which are beneficial to the plant when produced during water deficit.

Transcription factors are investigated for improving plant properties and traits in transgenic plants. Reference is made to WO 02079403 of Mendel Biotechnology, Inc. which claims priority from U.S. application Ser. No. 09/823,676 (incorporated herein by reference) for a disclosure of a variety of *Arabidopsis thaliana* transcription factors including one identified as G1073 which are alleged to be useful for modifying plant biomass, for methods of building DNA constructs which express transcript factors, and for methods of producing transformed plants with DNA constructs which express transcription factors.

One of the goals of plant genetic engineering is to produce plants with agronomically, horticulturally or economically important traits including tolerance to any of a variety of environmental stresses such as water deficit. Many transgenic crop plants have recombinant DNA that confers herbicide and/or pest resistance traits. Incorporation of additional recombinant DNA for conferring crop improvement traits in crop plants presents a challenge of using DNA constructs of increased complexity.

SUMMARY OF THE INVENTION

We have discovered that transcription factors G1073 and homologs (G1073 transcription factors) are useful for imparting enhanced resistance and/or tolerance to water deficit in transgenic plants. The present invention is directed to DNA which encode at least a functional part of a G1073 transcription factor which is useful in transgenic plants for enhancing yield when the plants are subjected to water deficit. One aspect of this invention provides methods for providing transgenic plants with an enhanced resistance and/or tolerance to water deficit. More particularly the method comprises transforming plants with recombinant DNA construct comprising DNA which encodes at least a functional part of a G1073 transcription factor, e.g. which imparts resistance to and/or tolerance to water deficit. Another aspect of the invention provides transgenic seed for growing a plant which is resistant to water deficit as compared to wild type wherein the genome of said seed comprises recombinant DNA which expresses at least a functional part of such a G1073 transcription factor, e.g. having an amino acid sequence comprising at least 50 contiguous amino acids of a G1073 transcription factor. In another aspect of the invention such transgenic seed has in its genome recombinant DNA which expresses a transcription factor polypeptide having an amino acid sequences which is at least 50% identical (and preferably of higher identity) with a synthetic consensus amino acid sequence from a conserved region of a G1073 transcription factor. In one aspect of the invention the recombinant DNA is exogenous DNA. In another aspect of the invention the DNA expressing a G1073 transcription factor is DNA from the *Arabidopsis thaliana* transcription factor G1073. In yet another aspect of the invention the DNA expressing a G1073 transcription factor is not derived from the *Arabidopsis thaliana* transcription factor G1073, but rather is derived from DNA expressing a homologous G1073 transcription factor from another species.

This invention also provides plants grown from such transgenic seed with recombinant DNA expressing a G1073 transcription factor. Transformed plants with tolerance and/or resistance to water deficit should inherently provide enhanced yield as compared to wild type plants which are stunted by or succumb to water deficit. One aspect of the invention provides transgenic plants with stacked engineered traits, e.g. a crop improvement trait provided by recombinant DNA expressing a G1073 transcription factor in combination with herbicide and/or pest resistance traits.

Another aspect of the invention provides hybrid corn with stacked engineered traits. One embodiment of such hybrid corn is the progeny of a transgenic ancestor corn plant having in its genome a recombinant DNA which expresses a G1073 transcription factor in combination with an herbicide and/or pest resistance trait. Embodiments of such hybrid corn have a transgenic male ancestor corn plant which has in its genome recombinant DNA which confers herbicide resistance and/or pest resistance.

BRIEF DESCRIPTION OF THE DRAWINGS

FIG. 1 is an amino acid sequence alignment of:
(a) all of SEQ ID NO:7 representing conserved amino acid sequence in an *Arabidopsis* transcription factor denoted "G1067" which is disclosed in application Ser. No. 09/934,455;
(b) all of SEQ ID NO:8 representing conserved amino acid sequence in an *Arabidopsis* transcription factor denoted "G1073" which has the full amino acid sequence of SEQ ID NO:1;
(c) residues 1-59 and 67-106 of SEQ ID NO:9 representing conserved amino acid sequence in a cotton transcription factor which has the full amino acid sequence of SEQ ID NO:3;
(d) residues 1-59 and 69-108 of SEQ ID NO:10 representing conserved amino acid sequence in a rice transcription factor which has the full amino acid sequence of SEQ ID NO:2; and
(e) all of SEQ ID NO: 11 which is a consensus representation of those conserved amino acid sequences.

DETAILED DESCRIPTION OF THE INVENTION

As used herein a "G1073 transcription factor" means a protein which is expressed by DNA of SEQ ID NO:4-6 and a protein having the amino acid sequence of SEQ ID NO:1-3 and a protein having the conserved amino acid sequence of SEQ ID NO:7-10 and a protein having the consensus amino acid sequence of SEQ ID NO:11 and a homologue protein from another species and parts of such proteins that function to provide the water-deficit-tolerance trait exhibited in *Arabidopsis thaliana*, e.g. in the assay illustrated in the example below.

As used herein "water deficit" is a plant condition characterized by water potential in a plant tissue of less than −0.7 megapascals (MPa), e.g. −0.8 Mpa. Water potential in maize is conveniently measured by clamping a leaf segment in a pressurizable container so that a cut cross section of leaf is open to atmospheric pressure. Gauge pressure (above atmospheric pressure) on the contained leaf section is increased until water begins to exude from the atmospheric-pressure-exposed cross section; the gauge pressure at incipient water exudation is reported as negative water potential in the plant tissue, e.g. 7 bars of gauge pressure is reported as −0.7 MPa water potential. Water deficit can be induced by withholding water from plants for sufficient time that wild type plants are deleteriously affected, e.g. as manifested by reduced yield, stunted growth, retarded development, death or the like. The plants of this invention show a remarkable risibility after periods of water deficit that are adverse to wild type plants.

As used herein "yield" of a crop plant means the production of a crop, e.g. shelled corn kernels or soybean or cotton fiber, per unit of production area, e.g. in bushels per acre or metric tons per hectare, often reported on a moisture adjusted basis, e.g. corn is typically reported at 15.5% moisture. Moreover a bushel of corn is defined by law in the State of Iowa as 56 pounds by weight, a useful conversion factor for corn yield is: 100 bushels per acre is equivalent to 6.272 metric tons per hectare. Other measurements for yield are in common practice. As used herein a "transgenic" organism, e.g. plant or seed, is one whose genome has been altered by the incorporation of exogenous genetic material or additional copies of native genetic material, e.g. by transformation or recombination of the organism or an ancestor organism. Transgenic plants include progeny plants of an original plant derived from a transformation process including progeny of breeding transgenic plants with wild type plants or other transgenic plants. Crop plants of interest in the present invention include, but are not limited to soy, cotton, canola, maize, wheat, sunflower, sorghum, alfalfa, barley, millet, rice, tobacco, fruit and vegetable crops, and turfgrass.

As used herein an "herbicide resistance" trait is a characteristic of a transgenic plant that is resistant to dosages of an herbicide that is typically lethal to a progenitor plant. Such herbicide resistance can arise from a natural mutation or more typically from incorporation of recombinant DNA that confers herbicide resistance. Herbicides for which resistance is useful in a plant include glyphosate herbicides, phosphinothricin herbicides, oxynil herbicides, imidazolinone herbicides, dinitroaniline herbicides, pyridine herbicides, sulfonylurea herbicides, bialaphos herbicides, sulfonamide herbicides and gluphosinate herbicides. To illustrate that the production of transgenic plants with herbicide resistance is a capability of those of ordinary skill in the art reference is made to U.S. patent application publications 2003/0106096A1 and 2002/0112260A1 and U.S. Pat. Nos. 5,034,322; 6,107,549 and 6,376,754, all of which are incorporated herein by reference.

As used herein an "pest resistance" trait is a characteristic of a transgenic plant is resistant to attack from a plant pest such as a virus, a nematode, a larval insect or an adult insect that typically is capable of inflicting crop yield loss in a progenitor plant. Such pest resistance can arise from a natural mutation or more typically from incorporation of recombinant DNA that confers pest resistance. For insect resistance, such recombinant DNA can, for example, encode an insect lethal protein such as a delta endotoxin of *Bacillus thuringiensis* bacteria or be transcribed to a dsRNA targeted for suppression of an essential gene in the insect. To illustrate that the production of transgenic plants with pest resistance is a capability of those of ordinary skill in the art reference is made to U.S. Pat. Nos. 5,250,515 and 5,880,275 which disclose plants expressing an endotoxin of *Bacillus thuringiensis* bacteria, to U.S. Pat. No. 6,506,599 which discloses control of invertebrates which feed on transgenic plants which express dsRNA for suppressing a target gene in the invertebrate, to U.S. Pat. No. 5,986,175 which discloses the control of viral pests by transgenic plants which express viral replicase, and to U.S. Patent Application Publication 2003/0150017 A1 which discloses control of pests by a transgenic plant which express a dsRNA targeted to suppressing a gene in the pest, all of which are incorporated herein by reference.

SEQ ID NO: 1 provides the amino acid sequence of *Arabidopsis thaliana* transcription factor G1073, which are disclosed in U.S. application Ser. No. 09/823,676, filed Mar. 26, 2001, incorporated herein by reference.

SEQ ID NO:2 provides the amino acid sequence of part of the rice (*Oryza sativa*) polypeptide which is a homolog of the *Arabidopsis thaliana* G1073 transcription factor.

SEQ ID NO:3 provides the amino acid sequence of part of the cotton (*Gossypium hirsutum*) polypeptide which is a homolog of the *Arabidopsis thaliana* G1073 transcription factor.

SEQ ID NO:4 provides DNA from the gene encoding an *Arabidopsis thaliana* G1073 transcription factor of SEQ ID NO:1.

SEQ ID NO:5 provides DNA from the gene encoding a rice transcription factor of SEQ ID NO:2.

SEQ ID NO:6 provides DNA from the gene encoding a cotton transcription factor of SEQ ID NO:3.

SEQ ID NO:7 provides a conserved region of the amino acid sequence of the *Arabidopsis thaliana* transcription factor G1067 which is disclosed in U.S. application Ser. No. 09/934,455, incorporated herein by reference.

SEQ ID NO: 8 provides a conserved region of the amino acid sequence of the *Arabidopsis thaliana* transcription factor G1073 (SEQ ID NO:1).

SEQ ID NO:9 provides a conserved region of the amino acid sequence of the cotton transcription factor (SEQ ID NO:3).

SEQ ID NO:10 provides a conserved region of the amino acid sequence of the rice transcription factor (SEQ ID NO:2).

SEQ ID NO:11 is an synthetic consensus amino acid sequence developed from alignment of the conserved region of SEQ ID NO: 7 through 10. The alignment is illustrated in FIG. 1.

SEQ ID NO: 12 provides DNA from the gene encoding an *Arabidopsis thaliana* G1067 transcription factor, a conserved region of which is SEQ ID NO:7.

Polynucleotides of the present invention are DNA that is used to impart the desired agronomic trait, e.g. such biological properties by providing for enhanced protein activity in a transgenic plants by overexpression of the polynucleotide, e.g. with a constitutive promoter or a promoter which is active during water deficit.

Protein and Polypeptide Molecules—Proteins of the present invention are whole proteins or at least a sufficient portion of the protein to impart the relevant biological activity of the protein, e.g. resistance and/or tolerance to water deficit in transgenic plants as compared to wild type, as provided by constitutive expression of the *Arabidopsis thaliana* G1073 transcription factor or a functionally homologous transcription factor. The term "protein" also includes molecules consisting of one or more polypeptide chains. Thus, a polypeptide useful in the present invention may constitute an entire gene product or one or more functional portion of a natural protein which provides the agronomic trait of this invention, i.e. enhanced yield despite exposure to, water deficit.

Homologs of the polypeptides of the present invention may be identified by comparison of the amino acid sequence of the polypeptide to amino acid sequences of polypeptides from the same or different plant sources, e.g. manually or by using known homology-based search algorithms such as those commonly known and referred to as BLAST, FASTA, and Smith-Waterman.

A further aspect of the invention comprises functional homolog proteins which differ in one or more amino acids from those of a polypeptide provided herein as the result of one or more of the well-known conservative amino acid substitutions, e.g. valine is a conservative substitute for alanine and threonine is a conservative substitute for serine. Conservative substitutions for an amino acid within the native polypeptide sequence can be selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Naturally conservative amino acids substitution groups are: valine-leucine, valine-isoleucine, phenylalanine-tyrosine, lysine-arginine, alanine-valine, aspartic acid-glutamic acid, and asparagine-glutamine. A further aspect of the invention comprises polypeptides which differ in one or more amino acids from those of a described protein sequence as the result of deletion or insertion of one or more amino acids in a native sequence.

Polypeptides of the present invention that are variants of the polypeptides provided herein will generally demonstrate significant identity with the polypeptides provided herein. Of particular interest are polypeptides having at least 50% sequence identity, more preferably at least about 70% sequence identity or higher, e.g. at least about 80% sequence identity with (a) an synthetic consensus amino acid sequence of SEQ ID NO:11 or (b) a conserved amino acid region of SEQ ID NO: 7 through 10 or (c) an amino acid sequence of SEQ ID NO:1 through 3, or (d) other functional homologs of any polypeptide identified in (a) through (c). Of course useful polypeptides also include those with higher identity to such a polypeptide sequence, e.g. 90%, to 100% identity. Other polypeptides of interest have at least 50 or more, e.g. at least 60 or 70 of the amino acids of a conserved segment of the transcription factors proteins as defined by SEQ ID NO:7 through 10 and the synthetic consensus amino acid sequence of SEQ ID NO:11. Of course useful polypeptides also include those with higher percentage of the amino acids in an protein segment of SEQ ID NO:7 thorough 11.

Recombinant DNA Constructs—The present invention contemplates the use of polynucleotides which encode a protein effective for imparting resistance and/or tolerance to water deficit in plants. Such polynucleotides are assembled in recombinant DNA constructs using methods known to those of ordinary skill in the art. A useful technology for building DNA constructs and vectors for transformation is the GATEWAY™ cloning technology (available from Invitrogen Life Technologies, Carlsbad, Calif.) uses the site specific recombinase LR cloning reaction of the Integrase/att system from bacteriophage lambda vector construction, instead of restriction endonucleases and ligases. The LR cloning reaction is disclosed in U.S. Pat. Nos. 5,888,732 and 6,277,608, U.S. Patent Application Publications 2001283529, 2001282319 and 20020007051, all of which are incorporated herein by reference. The GATEWAY™ Cloning Technology Instruction Manual which is also supplied by Invitrogen also provides concise directions for routine cloning of any desired RNA into a vector comprising operable plant expression elements.

Transgenic DNA constructs used for transforming plant cells will comprise the heterologous DNA which one desires to introduced into and a promoter to express the heterologous DNA in the host maize cells. As is well known in the art such constructs typically also comprise a promoter and other regulatory elements, 3' untranslated regions (such as polyadenylation sites), transit or signal peptides and marker genes elements as desired. For instance, see U.S. Pat. Nos. 5,858,642 and 5,322,938 which disclose versions of the constitutive promoter derived from cauliflower mosaic virus (CaMV35S), U.S. Pat. No. 6,437,217 which discloses a maize RS81 promoter, U.S. Pat. No. 5,641,876 which discloses a rice actin promoter, U.S. Pat. No. 6,426,446 which discloses a maize RS324 promoter, U.S. Pat. No. 6,429,362 which discloses a maize PR-1 promoter, U.S. Pat. No. 6,232,526 which discloses a maize A3 promoter, U.S. Pat. No. 6,177,611 which discloses constitutive maize promoters, U.S. Pat. No. 6,433,252 which discloses a maize L3 oleosin promoter, U.S. Pat. No. 6,429,357 which discloses a rice actin 2 promoter and intron, U.S. Pat. No. 5,837,848 which discloses a root specific promoter, U.S. Pat. No. 6,084,089 which discloses cold inducible promoters, U.S. Pat. No. 6,294,714 which discloses light inducible promoters, U.S. Pat. No. 6,140,078 which discloses salt inducible promoters, U.S. Pat. No. 6,252,138 which discloses pathogen inducible promoters, U.S. Pat. No. 6,175,060 which discloses phosphorus deficiency inducible promoters, U.S. Patent Application Publication 2002/0192813A1 which discloses 5', 3' and intron elements useful in the design of effective plant expression vectors, U.S. patent application Ser. No. 09/078,972 which discloses a coixin promoter, U.S. patent application Ser. No. 09/757,089 which discloses a maize chloroplast aldolase promoter, all of which are incorporated herein by reference.

In many aspects of the invention it is preferred that the promoter element in the DNA construct should be capable of causing sufficient expression to result in the production of an effective amount of the transcription factor in water deficit conditions. Such promoters can be identified and isolated from the regulatory region of plant genes which are over expressed in water deficit conditions. Specific water-deficit-inducible promoters for use in this invention are derived from the 5' regulatory region of genes identified as a heat shock protein 17.5 gene (HSP17.5), an HVA22 gene (HVA22), and a cinnamic acid 4-hydroxylase (CA4H) gene (CA4H) of *Zea maize*. Such water-deficit-inducible promoters are disclosed in U.S. provisional application Ser. No. 60/435,987, filed Dec. 20, 2002, incorporated herein by reference.

In general it is preferred to introduce heterologous DNA randomly, i.e. at a non-specific location, in the plant genome. In special cases it may be useful to target heterologous DNA insertion in order to achieve site specific integration, e.g. to replace an existing gene in the genome. In some other cases it may be useful to target a heterologous DNA integration into the genome at a predetermined site from which it is known that gene expression occurs. Several site specific recombination systems exist which are known to function implants include cre-lox as disclosed in U.S. Pat. No. 4,959,317 and FLP-FRT as disclosed in U.S. Pat. No. 5,527,695, both incorporated herein by reference.

Constructs and vectors may also include a transit peptide for targeting of a gene target to a plant organelle, particularly to a chloroplast, leucoplast or other plastid organelle. For a description of the use of a chloroplast transit peptide see U.S. Pat. No. 5,188,642, incorporated herein by reference.

In practice DNA is introduced into only a small percentage of target cells in any one experiment. Marker genes are used to provide an efficient system for identification of those cells that are stably transformed by receiving and integrating a transgenic DNA construct into their genomes. Preferred marker genes provide selective markers which confer resistance to a selective agent, such as an antibiotic or herbicide. Potentially transformed cells are exposed to the selective agent. In the population of surviving cells will be those cells where, generally, the resistance-conferring gene has been integrated and expressed at sufficient levels to permit cell survival. Cells may be tested further to confirm stable integration of the exogenous DNA. Useful selective marker genes include those conferring resistance to antibiotics such as kanamycin (nptII), hygromycin B (aph IV) and gentamycin (aac3 and aacC4) or resistance to herbicides such as glufosinate (bar or pat) and glyphosate (EPSPS). Examples of such selectable are illustrated in U.S. Pat. Nos. 5,550,318; 5,633,435; 5,780,708 and 6,118,047, all of which are incorporated herein by reference. Screenable markers which provide an ability to visually identify transformants can also be employed, e.g., a gene expressing a colored or fluorescent protein such as a luciferase or green fluorescent protein (GFP) or a gene expressing a beta-glucuronidase or uidA gene (GUS) for which various chromogenic substrates are known.

Transformation Methods and Transgenic Plants—Methods and compositions for transforming plants by introducing a transgenic DNA construct into a plant genome in the practice of this invention can include any of the well-known and demonstrated methods. Preferred methods of plant transformation are microprojectile bombardment as illustrated in U.S. Pat. Nos. 5,015,580; 5,550,318; 5,538,880; 6,160,208; 6,399,861 and 6,403,865 and *Agrobacterium*-mediated transformation as illustrated in U.S. Pat. Nos. 5,635,055; 5,824,877; 5,591,616; 5,981,840 and 6,384,301, all of which are incorporated herein by reference. See also U.S. application Ser. No. 09/823,676, incorporated herein by reference, for a description of vectors, transformation methods, and production of transformed *Arabidopsis thaliana* plants where transcription factors such as G1073 are constitutively expressed by a CaMV35S promoter.

Transformation methods of this invention to provide plants with enhanced environmental stress tolerance are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Those cells which are capable of proliferating as callus also are recipient cells for genetic transformation. Practical transformation methods and materials for making transgenic plants of this invention, e.g. various media and recipient target cells, transformation of immature embryos and subsequent regeneration of fertile transgenic plants are disclosed in U.S. Pat. No. 6,194,636 and U.S. patent application Ser. No. 09/757,089, which are incorporated herein by reference.

The seeds of this invention can be harvested from fertile transgenic plants and be used to grow progeny generations of transformed plants of this invention including hybrid plants line comprising the DNA construct expressing a transcription factor which provides the benefits of resistance and/or tolerance to water deficit.

Breeding of Transgenic Plants

In addition to direct transformation of a plant with a recombinant DNA construct, transgenic plants can be prepared by crossing a first plant having a recombinant DNA construct with a second plant lacking the construct. For example, recombinant DNA can be introduced into a plant line that is amenable to transformation to produce a transgenic plant which can be crossed with a second plant line to introgress the recombinant DNA into the second plant line.

In one aspect of the invention a transgenic plant with recombinant DNA conferring a crop improvement trait is crossed with a transgenic plant having recombinant DNA conferring herbicide and/or pest resistance to produce progeny plants having recombinant DNA that confers both the crop improvement trait and the herbicide and/or pest resistance trait. Preferably, in such breeding for combining traits the transgenic plant donating the crop improvement trait is a female line and the transgenic plant donating the herbicide and/or pest resistance trait is a male line. The progeny of this cross will segregate such that some of the plant will carry the DNA for both parental traits and some will carry DNA for one parental trait; such plants can be identified by markers associated with parental recombinant DNA Progeny plants carrying DNA for both parental traits can be crossed back into the female parent line multiple times, e.g. usually 6 to 8 generations, to produce a progeny plant with substantially the same genotype as one original transgenic parental line but for the recombinant DNA of the other transgenic parental line.

In yet another aspect of the invention hybrid transgenic seed, e.g. a hybrid transgenic corn seed, is produced by crossing a female transgenic corn line containing recombinant DNA conferring a crop improvement trait with a male transgenic corn line containing recombinant DNA conferring herbicide and/or pest resistance. In a preferred aspect of this invention hybrid transgenic corn seed is produced by crossing a female transgenic corn line with recombinant DNA conferring both a crop improvement trait and herbicide resistance with a male transgenic corn line with recombinant DNA conferring both herbicide resistance and pest resistance.

Having now generally described the invention, the same will be more readily understood through reference to the following example which is provided by way of illustration, and is not intended to be limiting of the present invention, unless specified.

EXAMPLES

These examples illustrates the use of a polynucleotide encoding transcription factor G1073 to provide a transgenic plant exhibiting enhanced tolerance for and/or resistance to growing conditions of water deficit.

Transgenic *Arabidopsis thaliana* was prepared with an exogenous DNA construct comprising a constitutive promoter of CaMV 35S operably linked to a polynucleotide of SEQ ID NO: 12 encoding *Arabidopsis thaliana* transcription factor G1073 of SEQ ID NO:1. Transgenic and wild type plants were potted in garden soil in a controlled environmental growth chamber in a 12 hour light/dark cycle. When the plants were at the early flowering stage, they were screened for water-deficit tolerance. Water was withheld until the wild type plants began wilting. Carbon dioxide assimilation rates were measured at growth and saturated conditions. Growth conditions were light at 200 μmol $m^{-2}$ $s^{-1}$ and 350 ppm $CO_2$. Saturating conditions were light at 1000 μmol $m^{-2}$ $s^{-1}$ and 1000 ppm $CO_2$. Wild type plants had smaller stomata conductance and lower $CO_2$ assimilation rates than did the transgenic plants.

Transgenic soybean was prepared with an exogenous DNA construct comprising a constitutive promoter CaMV35S operably linked to a polynucleotide of SEQ ID NO: 12 encoding *Arabidopsis thaliana* transcription factor G1073 of SEQ ID NO:1. When grown in water-deficit assay conditions the transgenic soybean showed enhanced resistance and/or tolerance to water deficit as compared to wild type.

Transgenic corn was prepared with an exogenous DNA construct comprising a constitutive promoter of the rice actin 1 gene operably linked to a polynucleotide of SEQ ID NO: 12 encoding *Arabidopsis thaliana* transcription factor G1073 of SEQ ID NO:1. Transgenic corn exhibited various enhance traits, e.g. increased biomass, increased seed oil, increased yield and the ability to utilize high levels of nitrogen.

We claim:

1. A transgenic seed for growing a transgenic plant having in its genome recombinant DNA which expresses a transcription factor comprising the 336 amino acid sequence encoded by SEQ ID NO:5, wherein said transcription factor imparts tolerance to water deficit in a transgenic plant grown from said seed.

2. The transgenic seed of claim 1, wherein said recombinant DNA comprises the sequence of SEQ ID NO:5.

3. The transgenic seed of claim 1 wherein said plant is a crop selected from the group consisting of a variety of maize, soybean, cotton, rice, wheat, canola and turfgrass.

4. A transgenic-water-deficit tolerant plant grown from a seed of claim 1.

5. A method for improving the yield of a crop plant variety as compared to said crop variety lacking recombinant DNA expressing a G1073 transcription factor when said crop varieties are grown in a water deficient environment, said method comprising inserting into the genome of said variety recombinant DNA which expresses a transcription factor comprising the 336 amino acid sequence encoded by SEQ ID NO:5.

6. A method of improving a hybrid crop plant by crossing a first crop with a second crop wherein pollen from said first crop contains recombinant DNA which expresses a transcription factor comprising the 336 amino acid sequence encoded by SEQ ID NO:5.

7. The method of claim 6 wherein one of said crops comprises recombinant DNA which expresses a protein that confers at least one of an herbicide resistance trait or a pest resistance trait.

8. A hybrid corn seed which is the progeny of
(a) a transgenic female ancestor corn plant having in its genome a recombinant DNA which expresses a transcription factor comprising the 336 amino acid sequence encoded by SEQ ID NO:5;
(b) a transgenic male ancestor corn plant having in its genome a recombinant DNA which confers at least one of an herbicide resistance trait or a pest resistance trait.

9. The hybrid corn seed of claim 8 wherein said transgenic female ancestor corn plant further has in its genome recombinant DNA which confers herbicide resistance.

10. The hybrid corn seed of claim 9 wherein said transgenic male ancestor corn plant has in its genome recombinant DNA which confers both herbicide resistance and insect resistance.

11. The hybrid corn seed of claim 9 having resistance to at least one herbicide selected from the group consisting of a glyphosate herbicide, a phosphinothricin herbicide, an oxynil herbicide, an imidazolinone herbicide, a dinitroaniline herbicide, a pyridine herbicide, a sulfonylurea herbicide, a bialaphos herbicide, a sulfonamide herbicide and a gluphosinate herbicide.

* * * * *

```
                       SEQUENCE LISTING

<160> NUMBER OF SEQ ID NOS: 12

<210> SEQ ID NO 1
<211> LENGTH: 270
<212> TYPE: PRT
<213> ORGANISM: Arabidopsis thaliana

<400> SEQUENCE: 1

Met Glu Leu Asn Arg Ser Glu Ala Asp Glu Ala Lys Ala Glu Thr Thr
1               5                   10                  15

Pro Thr Gly Gly Ala Thr Ser Ser Ala Thr Ala Ser Gly Ser Ser Ser
            20                  25                  30

Gly Arg Arg Pro Arg Gly Arg Pro Ala Gly Ser Lys Asn Lys Pro Lys
        35                  40                  45

Pro Pro Thr Ile Ile Thr Arg Asp Ser Pro Asn Val Leu Arg Ser His
    50                  55                  60

Val Leu Glu Val Thr Ser Gly Ser Asp Ile Ser Glu Ala Val Ser Thr
65                  70                  75                  80

Tyr Ala Thr Arg Arg Gly Cys Gly Val Cys Ile Ile Ser Gly Thr Gly
                85                  90                  95

Ala Val Thr Asn Val Thr Ile Arg Gln Pro Ala Ala Pro Ala Gly Gly
            100                 105                 110

Gly Val Ile Thr Leu His Gly Arg Phe Asp Ile Leu Ser Leu Thr Gly
        115                 120                 125

Thr Ala Leu Pro Pro Pro Ala Pro Pro Gly Ala Gly Gly Leu Thr Val
    130                 135                 140
```

-continued

Tyr Leu Ala Gly Gly Gln Gly Gln Val Val Gly Asn Val Ala Gly
145                 150                 155                 160

Ser Leu Ile Ala Ser Gly Pro Val Val Leu Met Ala Ser Phe Ala
            165                 170                 175

Asn Ala Val Tyr Asp Arg Leu Pro Ile Glu Glu Glu Thr Pro Pro
            180                 185                 190

Pro Arg Thr Thr Gly Val Gln Gln Gln Pro Glu Ala Ser Gln Ser
            195                 200                 205

Ser Glu Val Thr Gly Ser Gly Ala Gln Ala Cys Glu Ser Asn Leu Gln
            210                 215                 220

Gly Gly Asn Gly Gly Gly Val Ala Phe Tyr Asn Leu Gly Met Asn
225                 230                 235                 240

Met Asn Asn Phe Gln Phe Ser Gly Gly Asp Ile Tyr Gly Met Ser Gly
                245                 250                 255

Gly Ser Gly Gly Gly Gly Gly Ala Thr Arg Pro Ala Phe
            260                 265                 270

<210> SEQ ID NO 2
<211> LENGTH: 295
<212> TYPE: PRT
<213> ORGANISM: Oryza sativa

<400> SEQUENCE: 2

Met Glu His Ser Lys Met Ser Pro Asp Lys Ser Pro Val Gly Glu Gly
1               5                   10                  15

Asp His Ala Gly Gly Ser Gly Ser Gly Gly Val Gly Gly Asp His Gln
                20                  25                  30

Pro Ser Ser Ser Ala Met Val Pro Val Glu Gly Gly Ser Gly Ser Ala
            35                  40                  45

Gly Gly Ser Gly Ser Gly Gly Pro Thr Arg Arg Pro Arg Gly Arg Pro
50                  55                  60

Pro Gly Ser Lys Asn Lys Pro Lys Pro Pro Ile Ile Val Thr Arg Asp
65                  70                  75                  80

Ser Pro Asn Ala Leu His Ser His Val Leu Glu Val Ala Gly Gly Ala
                85                  90                  95

Asp Val Val Asp Cys Val Ala Glu Tyr Ala Arg Arg Arg Gly Arg Gly
            100                 105                 110

Val Cys Val Leu Ser Gly Gly Ala Val Val Asn Val Ala Leu Arg
            115                 120                 125

Gln Pro Gly Ala Ser Pro Pro Gly Ser Met Val Ala Thr Leu Arg Gly
130                 135                 140

Arg Phe Glu Ile Leu Ser Leu Thr Gly Thr Val Leu Pro Pro Pro Ala
145                 150                 155                 160

Pro Pro Gly Ala Ser Gly Leu Thr Val Phe Leu Ser Gly Gly Gln Gly
            165                 170                 175

Gln Val Ile Gly Gly Ser Val Val Gly Pro Leu Val Ala Ala Gly Pro
            180                 185                 190

Val Val Leu Met Ala Ala Ser Phe Ala Asn Ala Val Tyr Glu Arg Leu
            195                 200                 205

Pro Leu Glu Gly Glu Glu Glu Val Ala Pro Ala Ala Gly Gly
            210                 215                 220

Glu Ala Gln Asp Gln Val Ala Gln Ser Ala Gly Pro Pro Gly Gln Gln
225                 230                 235                 240

Pro Ala Ala Ser Gln Ser Ser Gly Val Thr Gly Gly Asp Gly Thr Gly
            245                 250                 255

```
Gly Ala Gly Gly Met Ser Leu Tyr Asn Leu Ala Gly Asn Val Gly
            260                 265                 270

Tyr Gln Leu Pro Gly Asp Asn Phe Gly Gly Trp Ser Gly Ala Gly Ala
                275                 280                 285

Gly Gly Val Arg Pro Pro Phe
        290                 295

<210> SEQ ID NO 3
<211> LENGTH: 230
<212> TYPE: PRT
<213> ORGANISM: Gossypium hirsutum

<400> SEQUENCE: 3

Ala Phe Gly Ser His Tyr Lys Leu Trp Arg Arg Ser Thr Thr Ser Gly
1               5                   10                  15

Lys Lys Pro Arg Gly Arg Pro Ala Gly Ser Lys Asn Lys Pro Lys Ser
            20                  25                  30

Pro Ile Ile Val Ala Arg Asp Ser Pro Asn Ser Leu Arg Ser His Val
        35                  40                  45

Leu Glu Ile Ser Ser Gly Ser Asp Ile Val Asp Ser Val Trp Gly Tyr
    50                  55                  60

Ala Arg Arg Arg Gly Arg Gly Val Cys Val Leu Ser Gly Thr Gly Ala
65                  70                  75                  80

Val Thr Asn Val Thr Leu Arg Gln Pro Ala Ala Pro Pro Gly Ser Val
                85                  90                  95

Val Thr Leu His Gly Arg Phe Glu Ile Leu Ser Leu Thr Gly Thr Ser
            100                 105                 110

Leu Pro Pro Pro Ala Pro Pro Gly Ala Gly Gly Leu Thr Val Tyr Leu
        115                 120                 125

Ala Gly Val Gln Gly Gln Val Val Gly Gly Ser Val Val Gly Pro Leu
    130                 135                 140

Met Ala Ser Gly Pro Val Val Leu Met Ala Ala Ser Phe Ala Asn Ala
145                 150                 155                 160

Val Tyr Asp Arg Leu Pro Leu Glu Glu Glu Asp Pro Pro Thr Val His
                165                 170                 175

Glu Gln Gln Pro Ala Ala Ser Gln Ser Ser Gly Leu Thr Gly Ser Gly
            180                 185                 190

Gly Gly Asn Asn Asn Asn Cys Gly Thr Thr Gly Thr Gly Val Gly Gly
        195                 200                 205

Gly Gly Gly Gly Val Pro Phe Tyr Asn Leu Gly Pro Asn Met Gly Thr
    210                 215                 220

Tyr Pro Phe Pro Gly Leu
225                 230

<210> SEQ ID NO 4
<211> LENGTH: 974
<212> TYPE: DNA
<213> ORGANISM: Arabidopsis thaliana

<400> SEQUENCE: 4 cccccgacc tgcctctaca gagacctgaa gattccagaa ccccacctga tcaaaaataa      60
catggaactt aacagatctg aagcagacga agcaaaggcc gagaccactc ccaccggtgg    120
agccaccagc tcagccacag cctctggctc ttcctccgga cgtcgtccac gtggtcgtcc    180
tgcaggttcc aaaaacaaac ccaaacctcc gacgattata actagagata gtcctaacgt    240
ccttagatca cacgttcttg aagtcacctc cggttcggac atatccgagg cagtctccac    300
```

-continued

```
ctacgccact cgtcgcggct gcggcgtttg cattataagc ggcacgggtg cggtcactaa      360
cgtcacgata cggcaacctg cggctccggc tggtggaggt gtgattaccc tgcatggtcg      420
gtttgacatt ttgtctttga ccggtactgc gcttccaccg cctgcaccac cgggagcagg      480
aggtttgacg gtgtatctag ccggaggtca aggacaagtt gtaggaggga atgtggctgg      540
ttcgttaatt gcttcgggac cggtagtgtt gatggctgct tcttttgcaa acgcagttta      600
tgataggtta ccgattgaag aggaagaaac cccaccgccg agaaccaccg gggtgcagca      660
gcagcagccg gaggcgtctc agtcgtcgga ggttacgggg agtggggccc aggcgtgtga      720
gtcaaacctc caaggtggaa atggtggagg aggtgttgct ttctacaatc ttggaatgaa      780
tatgaacaat tttcaattct ccgggggaga tatttacggt atgagcggcg gtagcggagg      840
aggtggtggc ggtgcgacta gacccgcgtt ttagagtttt agcgttttgg tgacaccttt      900
tgttgcgttt gcgtgtttga cctcaaacta ctaggctact agctatagcg gttgcgaaat      960
gcgaatatta ggtt                                                       974
```

<210> SEQ ID NO 5
<211> LENGTH: 1071
<212> TYPE: DNA
<213> ORGANISM: Oryza sativa

<400> SEQUENCE: 5

```
atggccggga tggaccctgg cgggggcggc gccggcgccg gcagctcacg gtacttccac       60
catctgctcc gaccgcagca gccgtcgccg ctgtcaccgc tgtcgccgac atcccatgtc      120
aagatggagc actccaagat gtcacccgac aagagccccg tgggcgaggg agatcacgcg      180
ggagggagtg gaagcggcgg cgtcggcggt gaccaccagc cgtcgtcgtc ggccatggtg      240
cccgtcgagg gtgcagcgg cagcgccggc ggtagtggct cgggtgggcc gacgcggcgc      300
ccgcgcgggc gcccgcccgg gtccaagaac aagccgaagc cgcccatcat cgtgacgcgc      360
gacagcccga acgcgctgca ctcgcacgtg ctcgaggtcg ccggcggcgc cgacgtcgtc      420
gactgcgtgg ccgagtacgc ccgccgccga gggcgcggcg tgtgcgtgct gagcggcggc      480
ggcgccgtcg tcaacgtggc gctgcggcag ccgggcgcgt cgccgccggg cagcatggtg      540
gccacgctgc ggggccggtt cgagatccta tctctcacgg gcacggtcct gccgcctccc      600
gcgccacccg gcgcgagcgg cctcaccgtg ttcctctccg gcggccaggg ccaggtgatc      660
ggcggcagcg tggtgggccc gctggtcgcc gcggggcccg tcgtcctgat ggcggcctca      720
ttcgcgaacg ccgtgtacga gcggctgccg ctggagggca aggaagagga ggtcgccgcg      780
cccgccgccg gaggcgaagc acaagatcaa gtggcacaat cagctggacc cccagggcag      840
caaccggcgc gtcacagtc ctccggcgtg acaggaggcg acggcaccgg cggcgccggt      900
ggcatgtcgc tctacaacct cgccgggaat gtgggaggct atcagctccc cggagacaac      960
ttcggaggtt ggagcggcgc cggcgccggc ggagtcaggc caccgttctg acccatgtct     1020
tagcatccag ttcaaaaatt ctccaaatta agaattgcgc agtgcagaag c              1071
```

<210> SEQ ID NO 6
<211> LENGTH: 693
<212> TYPE: DNA
<213> ORGANISM: Gossypium hirsutum

<400> SEQUENCE: 6

```
gcgttcggca gccactacaa gctctggagg aggagtacca cgtcgggaaa aaaacctaga       60
ggacgtccag cgggatccaa gaacaagccg aaatcaccca taatcgttgc tcgcgacagt      120
```

```
ccgaactcgt tgagatccca cgtgctcgaa atctcttccg gttcagacat agttgactcg    180
gtgtggggct acgcacggcg gcgcggccgt ggcgtttgtg tactcagcgg gaccggtgcc    240
gtcacgaatg tcacgttaag gcaaccggct gctccacctg gaagtgtcgt aacactacac    300
ggtcggttcg agatttttatc tttaaccggg acttctctcc caccgccagc accgcctgga    360
gctggtggat tgacggttta tctcgccggc gttcaaggtc aagtagtcgg aggaagcgtg    420
gtgggaccgt taatggcttc aggtccagtc gtattaatgg ctgcatcgtt cgccaatgca    480
gtttacgata ggttacctct cgaagaagaa gacccaccaa ccgttcacga caacaaccca    540
gcagcttcac aatcatccgg attaaccggc agtggcggcg aaacaacaa caactgtgga    600 acaaccggaa ccggcgtagg cggcggcggc ggcggggttc ctttctataa tttgggacca    660
aacatgggaa cttatccatt tccaggatta tga                                693
```

<210> SEQ ID NO 7
<211> LENGTH: 99
<212> TYPE: PRT
<213> ORGANISM: Arabidopsis thaliana
<400> SEQUENCE: 7

```
Ala Lys Pro Pro Ile Ile Val Thr Arg Asp Ser Pro Asn Ala Leu Arg
1               5                   10                  15

Ser His Val Leu Glu Val Ser Pro Gly Ala Asp Ile Val Glu Ser Val
            20                  25                  30

Ser Thr Tyr Ala Arg Arg Gly Arg Gly Val Ser Val Leu Gly Gly
        35                  40                  45

Asn Gly Thr Val Ser Asn Val Thr Leu Arg Gln Val Val Thr Leu His
    50                  55                  60

Gly Arg Phe Glu Ile Leu Ser Leu Thr Gly Thr Val Leu Pro Pro Pro
65                  70                  75                  80

Ala Pro Pro Gly Ala Gly Gly Leu Ser Ile Phe Leu Ala Gly Gly Gln
                85                  90                  95

Gly Gln Val
```

<210> SEQ ID NO 8
<211> LENGTH: 99
<212> TYPE: PRT
<213> ORGANISM: Arabidopsis thaliana
<400> SEQUENCE: 8

```
Pro Lys Pro Pro Thr Ile Ile Thr Arg Asp Ser Pro Asn Val Leu Arg
1               5                   10                  15

Ser His Val Leu Glu Val Thr Ser Gly Ser Asp Ile Ser Glu Ala Val
            20                  25                  30

Ser Thr Tyr Ala Thr Arg Arg Gly Cys Gly Val Cys Ile Ile Ser Gly
        35                  40                  45

Thr Gly Ala Val Thr Asn Val Thr Ile Arg Gln Val Ile Thr Leu His
    50                  55                  60

Gly Arg Phe Asp Ile Leu Ser Leu Thr Gly Thr Ala Leu Pro Pro Pro
65                  70                  75                  80

Ala Pro Pro Gly Ala Gly Gly Leu Thr Val Tyr Leu Ala Gly Gly Gln
                85                  90                  95

Gly Gln Val
```

<210> SEQ ID NO 9
<211> LENGTH: 107
<212> TYPE: PRT

-continued

<213> ORGANISM: Gossypium hirsutum

<400> SEQUENCE: 9

Pro Lys Ser Pro Ile Ile Val Ala Arg Asp Ser Pro Asn Ser Leu Arg
1               5                   10                  15

Ser His Val Leu Glu Ile Ser Ser Gly Ser Asp Ile Val Asp Ser Val
            20                  25                  30

Trp Gly Tyr Ala Arg Arg Arg Gly Arg Gly Val Cys Val Leu Ser Gly
        35                  40                  45

Thr Gly Ala Val Thr Asn Val Thr Leu Arg Gln Pro Ala Ala Pro Pro
    50                  55                  60

Gly Ser Val Val Thr Leu His Gly Arg Phe Glu Ile Leu Ser Leu Thr
65                  70                  75                  80

Gly Thr Ser Leu Pro Pro Ala Pro Pro Gly Ala Gly Gly Leu
                85                  90                  95

Val Tyr Leu Ala Gly Val Gln Gly Gln Val Val
            100                 105

<210> SEQ ID NO 10
<211> LENGTH: 109
<212> TYPE: PRT
<213> ORGANISM: Oryza sativa

<400> SEQUENCE: 10

Pro Lys Pro Pro Ile Ile Val Thr Arg Asp Ser Pro Asn Ala Leu His
1               5                   10                  15

Ser His Val Leu Glu Val Ala Gly Gly Ala Asp Val Val Asp Cys Val
            20                  25                  30

Ala Glu Tyr Ala Arg Arg Arg Gly Arg Gly Val Cys Val Leu Ser Gly
        35                  40                  45

Gly Gly Ala Val Val Asn Val Ala Leu Arg Gln Pro Gly Ala Ser Pro
    50                  55                  60

Pro Gly Ser Met Val Ala Thr Leu Arg Gly Arg Phe Glu Ile Leu Ser
65                  70                  75                  80

Leu Thr Gly Thr Val Leu Pro Pro Ala Pro Pro Gly Ala Ser Gly
                85                  90                  95

Leu Thr Val Phe Leu Ser Gly Gly Gln Gly Gln Val Ile
            100                 105

<210> SEQ ID NO 11
<211> LENGTH: 108
<212> TYPE: PRT
<213> ORGANISM: Artificial sequence
<220> FEATURE:
<223> OTHER INFORMATION: Synthetic construct
<220> FEATURE:
<221> NAME/KEY: unsure
<222> LOCATION: (1)..(108)
<223> OTHER INFORMATION: unsure at all Xaa locations
<220> FEATURE:
<221> NAME/KEY: UNSURE
<222> LOCATION: (3)..(3)
<223> OTHER INFORMATION: Xaa is Proline or Serine
<220> FEATURE:
<221> NAME/KEY: UNSURE
<222> LOCATION: (1)..(1)
<223> OTHER INFORMATION: Xaa is Alanine or Proline
<220> FEATURE:
<221> NAME/KEY: UNSURE
<222> LOCATION: (5)..(5)
<223> OTHER INFORMATION: Xaa is Isoleucine or Threonine
<220> FEATURE:
<221> NAME/KEY: UNSURE
<222> LOCATION: (7)..(7)

-continued

```
<223> OTHER INFORMATION: Xaa is Valine or Isoleucine
<220> FEATURE:
<221> NAME/KEY: UNSURE
<222> LOCATION: (8)..(8)
<223> OTHER INFORMATION: Xaa is Threonine or Alanine
<220> FEATURE:
<221> NAME/KEY: UNSURE
<222> LOCATION: (14)..(14)
<223> OTHER INFORMATION: Xaa is Alanine or Valine or Serine
<220> FEATURE:
<221> NAME/KEY: UNSURE
<222> LOCATION: (16)..(16)
<223> OTHER INFORMATION: Xaa is Arginine or Histidine
<220> FEATURE:
<221> NAME/KEY: UNSURE
<222> LOCATION: (22)..(22)
<223> OTHER INFORMATION: Xaa is Valine or Isoleucine
<220> FEATURE:
<221> NAME/KEY: UNSURE
<222> LOCATION: (23)..(23)
<223> OTHER INFORMATION: Xaa is Serine or Threonine or Alanine
<220> FEATURE:
<221> NAME/KEY: UNSURE
<222> LOCATION: (24)..(24)
<223> OTHER INFORMATION: Xaa is Proline or Serine or Glycine
<220> FEATURE:
<221> NAME/KEY: UNSURE
<222> LOCATION: (26)..(26)
<223> OTHER INFORMATION: Xaa is Alanine or Serine
<220> FEATURE:
<221> NAME/KEY: UNSURE
<222> LOCATION: (28)..(28)
<223> OTHER INFORMATION: Xaa is Isoleucine or Valine
<220> FEATURE:
<221> NAME/KEY: UNSURE
<222> LOCATION: (29)..(29)
<223> OTHER INFORMATION: Xaa is Valine or Serine
<220> FEATURE:
<221> NAME/KEY: UNSURE
<222> LOCATION: (30)..(30)
<223> OTHER INFORMATION: Xaa is Glutamic Acid or Aspartic Acid
<220> FEATURE:
<221> NAME/KEY: UNSURE
<222> LOCATION: (31)..(31)
<223> OTHER INFORMATION: Xaa is Serine or Alanine or Cysteine
<220> FEATURE:
<221> NAME/KEY: UNSURE
<222> LOCATION: (33)..(33)
<223> OTHER INFORMATION: Xaa is Serine or Tryptophan or Alanine
<220> FEATURE:
<221> NAME/KEY: UNSURE
<222> LOCATION: (34)..(34)
<223> OTHER INFORMATION: Xaa is Threonine or Glycine or Glutamic Acid
<220> FEATURE:
<221> NAME/KEY: UNSURE
<222> LOCATION: (37)..(37)
<223> OTHER INFORMATION: Xaa is Arginine or Threonine
<220> FEATURE:
<221> NAME/KEY: UNSURE
<222> LOCATION: (41)..(41)
<223> OTHER INFORMATION: Xaa is Arginine or Cysteine
<220> FEATURE:
<221> NAME/KEY: UNSURE
<222> LOCATION: (44)..(44)
<223> OTHER INFORMATION: Xaa is Serine or Cysteine
<220> FEATURE:
<221> NAME/KEY: UNSURE
<222> LOCATION: (45)..(45)
<223> OTHER INFORMATION: Xaa is Valine or Isoleucine
<220> FEATURE:
<221> NAME/KEY: UNSURE
<222> LOCATION: (46)..(46)
<223> OTHER INFORMATION: Xaa is Leucine or Isoleucine
<220> FEATURE:
<221> NAME/KEY: UNSURE
<222> LOCATION: (47)..(47)
<223> OTHER INFORMATION: Xaa is Glycine or Serine
<220> FEATURE:
<221> NAME/KEY: UNSURE
<222> LOCATION: (49)..(49)
```

```
<223> OTHER INFORMATION: Xaa is Asparagine or Threonine or Glycine
<220> FEATURE:
<221> NAME/KEY: UNSURE
<222> LOCATION: (51)..(51)
<223> OTHER INFORMATION: Xaa is Threonine or Alanine
<220> FEATURE:
<221> NAME/KEY: UNSURE
<222> LOCATION: (53)..(53)
<223> OTHER INFORMATION: Xaa is Serine or Threonine or Valine
<220> FEATURE:
<221> NAME/KEY: UNSURE
<222> LOCATION: (56)..(56)
<223> OTHER INFORMATION: Xaa is Threonine or Alanine
<220> FEATURE:
<221> NAME/KEY: UNSURE
<222> LOCATION: (57)..(57)
<223> OTHER INFORMATION: Xaa is Leucine or Isoleucine
<220> FEATURE:
<221> NAME/KEY: UNSURE
<222> LOCATION: (60)..(68)
<223> OTHER INFORMATION: Xaa can be any naturally occurring amino acid
      or can be none
<220> FEATURE:
<221> NAME/KEY: UNSURE
<222> LOCATION: (70)..(70)
<223> OTHER INFORMATION: Xaa is Valine or Isoleucine or Alanine
<220> FEATURE:
<221> NAME/KEY: UNSURE
<222> LOCATION: (73)..(73)
<223> OTHER INFORMATION: Xaa is Histidine or Arginine
<220> FEATURE:
<221> NAME/KEY: UNSURE
<222> LOCATION: (77)..(77)
<223> OTHER INFORMATION: Xaa is Glutamic Acid or Aspartic Acid
<220> FEATURE:
<221> NAME/KEY: UNSURE
<222> LOCATION: (85)..(85)
<223> OTHER INFORMATION: Xaa is Valine or Alanine or Serine
<220> FEATURE:
<221> NAME/KEY: UNSURE
<222> LOCATION: (95)..(95)
<223> OTHER INFORMATION: Xaa is Glycine or Serine
<220> FEATURE:
<221> NAME/KEY: UNSURE
<222> LOCATION: (98)..(98)
<223> OTHER INFORMATION: Xaa is Serine or Threonine
<220> FEATURE:
<221> NAME/KEY: UNSURE
<222> LOCATION: (99)..(99)
<223> OTHER INFORMATION: Xaa is Isoleucine or Valine
<220> FEATURE:
<221> NAME/KEY: UNSURE
<222> LOCATION: (100)..(100)
<223> OTHER INFORMATION: Xaa is Phenylalanine or Tyrosine
<220> FEATURE:
<221> NAME/KEY: UNSURE
<222> LOCATION: (104)..(104)
<223> OTHER INFORMATION: Xaa is Glycine or Valine

<400> SEQUENCE: 11

Xaa Lys Xaa Pro Xaa Ile Xaa Xaa Arg Asp Ser Pro Asn Xaa Leu Xaa
  1               5                  10                  15

Ser His Val Leu Glu Xaa Xaa Xaa Gly Xaa Asp Xaa Xaa Xaa Xaa Val
             20                  25                  30

Xaa Xaa Tyr Ala Xaa Arg Arg Gly Xaa Gly Val Xaa Xaa Xaa Xaa Gly
         35                  40                  45

Xaa Gly Xaa Val Xaa Asn Val Xaa Xaa Arg Gln Xaa Xaa Xaa Xaa Xaa
     50                  55                  60

Xaa Xaa Xaa Xaa Val Xaa Thr Leu Xaa Gly Arg Phe Xaa Ile Leu Ser
 65                  70                  75                  80

Leu Thr Gly Thr Xaa Leu Pro Pro Pro Ala Pro Pro Gly Ala Xaa Gly
             85                  90                  95

Leu Xaa Xaa Xaa Leu Ala Gly Xaa Gln Gly Gln Val
```

-continued

<210> SEQ ID NO 12
<211> LENGTH: 1473
<212> TYPE: DNA
<213> ORGANISM: Arabidopsis thaliana

<400> SEQUENCE: 12

```
tctcaagctt ctctctcctt tttttcccat agcacatcag aatcgctaaa tacgactcct      60
atgcaaagaa gaagctactt ctttctcttg ccctaattaa tctacctaac tagggtttcc     120
tcttaccttt catgagagag atcatttaac ataagtcacc tttttatat  cttttgcttc     180
gtctttaatt tagttctgtt cttggtctgt ttctatattt tgtcggcttg cgtaaccgat     240
cacaccttaa tgctttagct attgtttcct caaaatcatg agttttgact tctcgatctg     300
agttttcttt ttctctcttt acgctcttct tcacctagct accaatatat gaacgagcag     360
gatcaagaat cgagaaattg atttgagctg gcgaataagc agtggtggga tagggaatta     420
gtagatgcgg cggcgatgga aggcggttac gagcaaggcg gtggagcttc tagatacttc     480
cataacctct ttagaccgga gattcaccac caacagcttc aaccgcaggg cgggatcaat     540
cttatcgacc agcatcatca tcagcaccag caacatcaac aacaacaaca accgtcggat     600
gattcaagag aatctgacca ttcaaacaaa gatcatcatc aacagggtcg acccgattca     660
gacccgaata catcaagctc agcaccggga aaacgtccac gtggacgtcc accaggatct     720
aagaacaaag ccaagccacc gatcatagta actcgtgata gccccaacgc gcttagatct     780
cacgttcttg aagtatctcc tggagctgac atagttgaga gtgtttccac gtacgctagg     840
aggagaggga gaggcgtctc cgttttagga ggaaacggca ccgtatctaa cgtcactctc     900
cgtcagccag tcactcctgg aaatggcggt ggtgtgtccg gaggaggagg agttgtgact     960
ttacatggaa ggtttgagat tctttcgcta acggggactg ttttgccacc tcctgcaccg    1020
cctggtgccg gtggtttgtc tatatttta  gccggagggc aaggtcaggt ggtcggagga    1080
agcgttgtgg ctcccttat  tgcatcagct ccggttatac taatggcggc ttcgttctca    1140
aatgcggttt tcgagagact accgattgag gaggaggaag aagaaggtgg tggtggcgga    1200
ggaggaggag gaggagggcc accgcagatg caacaagctc catcagcatc tccgccgtct    1260
ggagtgaccg tcagggaca  gttaggaggt aatgtgggtg gttatgggtt ttctggtgat    1320
cctcatttgc ttggatgggg agctggaaca ccttcaagac cacctttta  attgaatttt    1380
aatgtccgga aatttatgtg tttttatcat cttgaggagt cgtcttcct  ttgggatatt    1440
tggtgtttaa tgtttagttg atatgcatat ttt                                  1473
```